United States Patent [19]

von der Eltz et al.

[11] Patent Number: 4,900,822

[45] Date of Patent: Feb. 13, 1990

[54] NEW HYDROLASE SUBSTRATES

[75] Inventors: Herbert von der Eltz; Hans-Joachim Guder, both of Weilheim; Klaus Mühlegger, Polling, all of Fed. Rep. of Germany

[73] Assignee: Boehringer Mannheim GmbH, Mannheim, Fed. Rep. of Germany

[21] Appl. No.: 135,843

[22] Filed: Dec. 21, 1987

[30] Foreign Application Priority Data

Dec. 24, 1986 [DE] Fed. Rep. of Germany ....... 3644401

[51] Int. Cl.$^4$ ........................................... C07D 265/38
[52] U.S. Cl. .................................... 544/102; 530/330; 530/331; 544/73; 544/104
[58] Field of Search ........................ 544/73, 102, 104; 530/330, 331

[56] References Cited

U.S. PATENT DOCUMENTS 3,642,997 2/1972 Shen et al. ...................... 544/102 X
4,719,097 1/1988 Mühlegger et al. ............. 544/102 X

FOREIGN PATENT DOCUMENTS 0157384 10/1985 European Pat. Off. .

OTHER PUBLICATIONS

Klein et al., Chemical Abstracts, vol. 104(1986) 168764s.

Primary Examiner—Richard L. Raymond
Attorney, Agent, or Firm—Felfe & Lynch

[57] ABSTRACT

Reagents for the determination of hydrolase comprises compounds of the formula

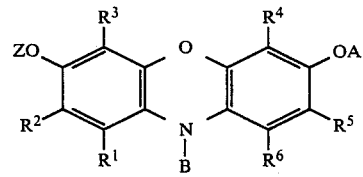

wherein Z is an organic or inorganic acid residue or a sugar residue, A is an organic or inorganic acid residue, and B is an organic acid residue. Each of $R^2$ and $R^5$, is hydrogen, halogen or lower alkyl. Each of $R^1$, $R^3$, $R^4$ and $R^6$, is hydrogen, halogen, cyano, lower alkyl, lower alkoxy, carboxyl, lower alkoxycarbonyl, carboxy lower alkyl or lower alkoxycarbonyl lower alkyl, or carboxamido groups optional substituted once or twice, or a radical of the formula $$-COO-(CH_2CH_2O)_n-R^7$$

in which $R^7$ is hydrogen or lower alkyl and n is a number from 1 to 4. Additionally, $R^6$ can be sulpho or nitro.

15 Claims, No Drawings

NEW HYDROLASE SUBSTRATES

The present invention is concerned with dihydroresorufin compounds which can be used as chromogenic and/or fluorogenic substrates for hydrolases, with processes for the preparation thereof, as well as with an appropriate reagent for the determination of hydrolases.

By hydrolases are generally understood enzymes which hydrolytically cleave bonds with the consumption of water. In clinical chemistry and in diagnosis, in recent years the determination of such hydrolases which cleave ester and ether bonds has, in particular, achieved importance. By way of example, there are to be mentioned esterases, such as the enzymes cleaving carboxyl esters which occur in leukocytes, and phosphatases, such as alkaline and acidic phosphatases which hydrolyse phosphoric acid esters, as well as glycosidases, such as galactosidases, glucosidases, mannosidases and amylases which cleave glycosidic bonds.

For the determination of the activity of hydrolases, the enzyme-containing sample is mixed with an appropriate substrate. The substrate is cleaved by the enzyme and one of the cleavage products is detected in appropriate manner. As substrates, there are often suitable the natural substrates of the enzymes to be detected. However, there are especially preferably used chromogenic or fluorogenic compounds in which one of the cleavage products is a radical which can be detected spectroscopically in the visible range or in the ultra-violet range or fluorometrically.

Previously known hydrolase substrates possess, as chromophore, for example phenol, naphthol or a derivative thereof. Such chromophores do not absorb at all in the visible wavelength range or only weakly. They can be measured ultra-violet spectrometrically in the short-wave range. Since the samples containing the enzyme to be measured mostly display a considerable inherent absorption in these wavelength ranges due to the presence of further component materials, the measurements can be very considerably disturbed. In order to avoid such disturbances, the cleavage products initially formed due to the action of a hydrolase, such as phenols or naphthols, can be oxidatively coupled with, for example, aminoantipyrine, or reacted with various diazonium salts to give azo-coloured materials and the coloured materials thus formed are then measured.

The determination of enzyme activities with fluorogenic substrates is widely used since, in comparison with photometric methods, the sensitivity of the fluorometric determinations is often increased by several powers of ten. In some cases, it is necessary to work with fluorogenic substrates, for example in the case of the investigation of enzymatic activity in cells with the use of automatic apparatus for cell differentiation (cytofluorometry), as well as in the case of the analysis of immobilised enzymes with flow-through fluorometry. In other cases, for example in the case of the determination of enzymatic labelling of test systems (enzyme immunoassays), the multiplication effect of the enzymatic catalysis is considerably increased by the use of fluorogenic substrates.

Hitherto known fluorogenic substrates for hydrolases possess, as fluorophores, for example fluoroscein, indoxyl, methylumbelliferrone or derivatives of these compounds. However, these compounds possess serious disadvantages for the kinetic analysis of complex systems. Thus, the fluorescein derivatives used as hydrolase substrates often already fluoresce themselves. Indoxyl derivatives, after their enzymatic cleavage, undergo a series of chemical changes which also complicate the kinetic analysis. Derivatives of methylumbelliferrone must be activated by ultra-violet light. The inherent fluorescence of biological and synthetic materials can hereby have a disturbing effect. Furthermore, the ultra-violet activation is expensive, especially in the case of laser optics. Most fluorogenic substrates give rise to reaction products which only have a low solubility so that they are not suitable for kinetic analyses of enzyme activities for which a good solubility of substrate and product is necessary.

Resorufin glycosides are known from Federal Republic of Germany patent specification No. 34 11 574 as special glycosidase substrates. Most are yellow coloured. After the enzymatic reaction, the products display a red colour.

In spite of the plurality of known chromogenic and fluorogenic substrates for the detection of hydrolases, a search is still being made for compounds which are broadly usable for the detection of the most varied hydrolases, possess a high sensitivity and are well suited for the most varied processes, for example ultra-violet photometric, visual and fluorimetric measurements.

Therefore, it is an object of the present invention to provide suitable hydrolase substrates which fulfil the above requirements.

The object is achieved by the new compounds according to the present invention which are cleaved by hydrolases into an acidic or hydroxyl part and into a dihydroresorufin derivative with at least one free hydroxyl group. The latter are readily water-soluble compounds which can easily be oxidised to resorufin compounds, which display a readily measurable absorption in the visible range and, furthermore, can easily be stimulated to fluoresce.

Thus, according to the present invention, there are provided compounds of the general formula:

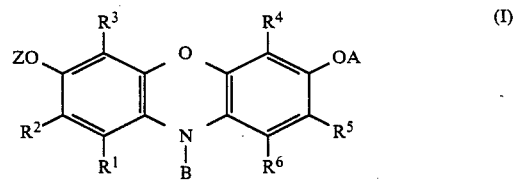

wherein Z is an organic or inorganic acid residue or a sugar residue, A is an organic or inorganic acid residue, B is an organic acid residue, $R^2$ and $R^5$, which can be the same or different, are hydrogen or halogen atoms or lower alkyl radicals, $R^1$, $R^3$, $R^4$ and $R^6$, which can be the same or different, are hydrogen or halogen atoms, cyano groups or lower alkyl, lower alkoxy, carboxyl, lower alkoxycarbonyl, carboxy lower alkyl or lower alkoxycarbonyl lower alkyl radicals or carboxamido groups optionally substituted once or twice or radicals of the general formula:

$$-COO-(CH_2CH_2O)_n-R^7$$

wherein $R^7$ is a hydrogen atom or a lower alkyl radical and n is a whole number of from 1 to 4, whereby $R^6$ can, in addition, also be a sulpho or nitro group.

By an inorganic acid residue in the definitions of A and Z are to be understood, in particular, ortho- and pyrophosphoric acid and sulphuric acid residues which are attached via an ester bond to the dihydroresorufin basic structure. The residues PO₃MM' and SO₃M are preferred and especially the residue PO₃MM', whereby, in the case of the free acids, M and M' are hydrogen atoms, whereas when the acids are present as salts, M and M' stand for alkali metal, alkaline earth metal or ammonium ions.

By alkali metal ions in the definition of M and M' are to be understood, in particular, lithium, sodium and potassium ions and alkaline earth metal ions are, in particular, magnesium, calcium and barium ions.

Ammonium ions in the definition of M and M' can be unsubstituted ammonium ions or ammonium ions substituted one or more times by lower alkyl or aryl lower alkyl radicals. The lower alkyl radicals are hereby to be understood to mean those with up to 5 carbon atoms, methyl and ethyl radicals being preferred. The substituents in substituted ammonium ions can be the same or different.

By an organic acid residue in the definition of Z are to be understood, in particular, alkanecarboxylic acid, amino acid and oligopeptide residues which are present bound with their carboxyl end as ester on the dihydroresorufin molecule.

Alkanecarboxylic acids in the definition of Z are compounds with up to 20 carbon atoms, acetic acid, propionic acid, butyric acid, palmitic acid and stearic acid being especially preferred. Besides saturated acid residues, Z can also be an unsaturated acid residue, for example an oleic acid, linoleic acid or linolenic acid residue.

The amino acid residues are preferably the residues of natural α-amino acids in their L- or D-form or also in their racemic form. The residues of glycine, alanine, valine, leucine, isoleucine, phenylalanine and thyrosine are especially preferred, the L-forms thereof being quite especially preferred. Free hydroxyl groups possibly present can be acylated and preferably acetylated.

By oligopeptide residues are to be understood, for example, di-, tri-, tetra- and pentapeptides and preferably di- and tripeptides, the amino acid components thereby preferably being the above-mentioned amino acids.

The amino groups of the amino acid and oligopeptide residues bound ester-like to the dihydroresorufin molecule can be present in the free or protected form. As protective groups there are here to be understood all conventional amino protective groups, especially acyl, oxycarbonyl, thiocarbonyl, sulpho, sulphino, vinyl, cyclohexenyl, phosphoryl and carbamoyl groups. Especially preferred amino protective groups include the tosyl, benzyloxycarbonyl and tert.-butoxycarbonyl radicals.

In the definition of B, an organic acid residue means, in particular, a lower alkylcarbonyl radical optionally substituted one or more times by hydroxyl, carboxyl and/or ammonium groups. The lower alkyl moiety of the lower alkylcarbonyl radical is a hydrocarbon radical containing up to 7 and preferably up to 5 carbon atoms. It can be saturated or unsaturated, straight-chained or branched.

Ammonium radicals are —NR⁺₃ radicals in which R can be a hydrogen atom or a lower alkyl or aryl lower alkyl radical. In principle, for the possible ammonium radicals there applies what was stated above with regard to the definitions of M and M'. A lower alkyl radical is one containing up to 5 carbon atoms, the methyl and ethyl radicals being preferred. A preferred aryl lower alkyl radical is the benzyl radical. The substituents R possibly present in the ammonium group can be the same or different, an especially preferred ammonium group being the trimethylammonium ion, —N(CH₃)₃⁺.

Especially preferred acid residues in the definition of B include the acetyl, oxalyl, malonyl, succinyl, glutaryl and carnityl radicals.

An organic acid residue in the definition of A includes the meanings given for B and Z. A can be an alkanecarboxylic acid residue or an amino acid or oligopeptide residue or a lower alkylcarbonyl radical optionally substituted one or more times by hydroxyl, carboxyl and/or ammonium. The individual definitions for the organic acid residues B and Z also apply to the organic acid residues in the definition of A. Compounds of general formula I in which A is an organic acid residue are especially preferred when A has the same meaning as B.

The sugar residue in the definition of Z can be a mono- or oligosaccharide. The sugar residue can be bound α- or β-glycosidically to the dihydroresorufin basic structure. Examples of preferred monosaccharides include galactose, glucose and mannose. However, as sugar residue, oligosaccharides can also be used. As oligosaccharides are meant, in particular, those which are made up of 2 to 10 and preferably of 2 to 7 monosaccharide units. Heptaoses are especially preferred.

In the definition of the radicals $R^1$–$R^7$, by halogen is to be understood fluorine, chlorine, bromine and iodine, chlorine and bromine being preferred.

The lower alkyl radical in the definition of $R^1$–$R^7$ contains up to 5 and preferably up to 3 carbon atoms, the methyl radical being especially preferred.

The lower alkoxy radical in the definition of $R^1$, $R^3$, $R^4$ and $R^6$ contains up to 5 and preferably up to 3 carbon atoms, the methoxy radical being especially preferred.

The lower alkoxy and the lower alkyl moieties of the lower alkoxycarbonyl, carboxy lower alkyl, as well as of the lower alkoxycarbonyl lower alkyl radicals in the definition of the substituents $R^1$, $R^3$, $R^4$ and $R^6$ also contain up to 5 and preferably up to 3 carbon atoms, the methoxy and methyl radicals being especially preferred.

The substituents of the carboxamido group include alkyl, alkoxyalkyl, carboxyalkyl and alkoxycarbonylalkyl radicals, the alkyl and alkoxy radicals thereby containing up to 5 and preferably up to 3 carbon atoms. In the case of a disubstituted carboxamide function, the two substituents can be joined to form a ring which can be interrupted by heteroatoms, for example oxygen, nitrogen and sulphur. In this sense, the morpholine radical is especially preferred as the amine part of the carboxamido group.

Preferred compounds of general formula (I) are those in which Z is a PO₃MM' or SO₃M group or an alkanecarboxylic acid, amino acid or oligopeptide residue, A is a PO₃MM' or SO₃M group or a lower alkylcarbonyl radical which is optionally substituted one or more times by carboxyl, hydroxyl and/or ammonium, or is a carboxyl-bound amino acid or oligopeptide residue, M and M' are hydrogen atoms or alkali metal, alkaline earth metal or ammonium ions and B is a lower alkylcarbonyl radical optionally substituted one or more times by carboxyl, hydroxyl and/or ammonium, and $R^1$–$R^7$ have the same meanings as above.

The compounds of general formula (I) are new. They can be prepared by known methods from resorufins of the general tautomeric formulae:

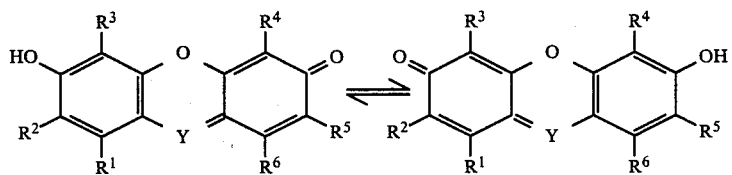

(IIa)    (IIb)

wherein $R^1-R^6$ have the same meanings as given in general formula (I) and Y is a nitrogen atom or an N→O group. Depending upon whether (a) A is different from Z and A is the same as B or
(b) A is the same as Z and A is different from B or
(c) A, B and Z are all different a differentiation can be made between three process variants.

For the synthesis of compounds of general formula (I) in which A is different from Z and A is the same as B, a compound of the general tautomeric formulae (IIa) and (IIb) is reacted with a compound of the general formula:

X—Z     (III)

in which Z has the meaning given in general formula (I) and X is a reactive group, to give a resorufin derivative of the tautomeric general formulae:

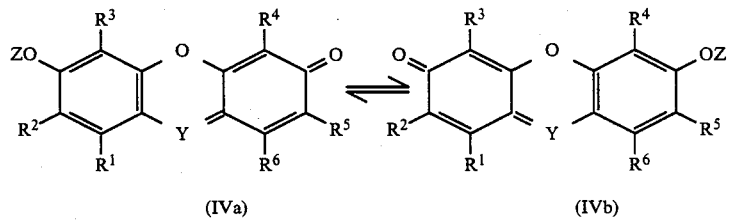

(IVa)    (IVb)

in which $R^1-R^6$, Y and Z have the above-given meanings, reduced and acylated by means of a compound of the general formula:

X—B     (V), in which B has the meaning given in general formula (I) and X is a reactive group.

Resorufins of general formulae (IIa) and (IIb) are the subject of European patent specification No. 0,156,347.

In the acylation reagent of general formula (III), Z has the meaning given in general formula (I). It is preferably an inorganic acid residue of the group orthophosphoric acid and sulphuric acid, alkanecarboxylic acid, amino acid and oligopeptide residues and sugar residues. Free amino and hydroxyl groups of amino acids, oligopeptide and sugar residues can hereby optionally be protected by appropriate, conventional protective groups which can subsequently be split off again under appropriate conditions after having carried out the last acylation step with X-A.

X is a reactive group which is able to enter into reaction with the phenolic hydroxyl group of the resorufin of general formula (IIa) or (IIb). The choice of the reactive group X depends upon the nature of the radical Z. If Z is a sugar residue, then X is preferably an acetyl radical or a halogen atom, which can be selected from the group fluorine, chlorine, bromine and iodine, chlorine, bromine and iodine being preferred.

The synthesis of resorufin glycosides of general formulae (IVa) and (IVb) in which Z is a sugar residue can be carried out according to the teachings of European patent specification No. 0,156,347.

When Z is an amino acid or peptide residue which is to be esterified with its carboxyl end with a resorufin of general formula (IIa) or (IIb), then the reactive group X can be any of the groups conventional in peptide chemistry. As reactive derivatives, there are used, for example, acid halides, preferably acid chlorides, or the mixed anhydrides or active esters usually employed in peptide syntheses. The same reactive groups can also be used for the binding of alkanecarboxylic acids to the resorufin structure.

When Z is an inorganic acid residue, resorufins of general formulae (IIa) and (IIb) are preferably reacted with the appropriate acid halides, especially acid chlorides.

For the synthesis of compounds of general formulae (IVa) and (IVb), in which Z is a $PO_3MM'$ residue, there can be used the process described in Federal Republic of Germany patent specification No. 35 34 927.

The reduction of the resorufin derivatives of general formulae (IVa) and (IVb) takes place hydrogenolytically, for example over palladium on carbon, or with a strong reducing agent, for example zinc powder, stannous, chloride or chromous acetate, or electrochemically. For the reduction, the resorufin derivative is heated for from 10 to 60 minutes under an atmosphere of hydrogen or with 2 to 10 and preferably with 2 to 6 equivalents of the strong reducing agent, preferably stannous chloride, in an appropriate solvent.

The subsequent acylation then takes place in the usual way with an acylation agent of the general formula:

X—B     (V)

wherein B has the meaning given in general formula (I) and X is a reactive group.

As acylation agents, there are preferred acid halides, anhydrides and esters, acid halides being especially preferred. The halogen atom is preferably selected from the group chlorine, bromine and iodine, chlorine and bromine being especially preferred.

The compounds of general formula (I) are preferably prepared in a one-pot process by the reductive acylation of resorufin derivatives of general formulae (IVa) and (IVb). For this purpose, the appropriate resorufin derivative is heated under reflux with 2 to 6 equivalents of the reducing agent in the presence of the acylation agent (X-B) in an appropriate solvent for a period of from 5 minutes to 3 hours or is stirred at ambient temperature for a period of from 4 to 16 hours.

Appropriate solvents are dipolar aprotic liquids or the acid corresponding to the acylation agent. Thus, for acetylation, there is used, for example, glacial acetic acid as solvent.

For the preparation of compounds of general formula (I) in which A is the same as Z and A is different from B, compounds of the general tautomeric general formulae (IIa) and (IIb), in which $R^1$–$R^6$ and Y have the above-given meanings, are reduced, acylated with a compound of the general formula:

X—B          (V), in which B has the meaning given in general formula (I) and X is a reactive group, the ester bond is subsequently selectively hydrolysed and then reacted with a compound of the general formula:

X—A          (VI)

in which A and X have the above-given meanings.

The reduction of resorufin derivatives of general formulae (IIa) and (IIb) can take place in the same way as has already been described for the reduction of resorufin derivatives of general formulae (IVa) and (IVb).

The acylation by means of a compound of general formula (V) takes place in the usual way. Preferred acylation agents include acid halides, acid anhydrides and esters, acid halides and acid anhydrides preferably being used. It is especially preferred to use acid chlorides of lower alkanecarboxylic acids containing up to 5 carbon atoms, acetyl chloride being quite especially preferred.

In a preferred process, the compounds of the general tautomeric formulae (IIa) and (IIb) are reductively acylated in a one-pot process. The appropriate resorufin derivative is, for this purpose, heated under reflux under an atmosphere of hydrogen, for example in the presence of palladium on charcoal, or with 2 to 6 equivalents of a strong reducing agent in the presence of the acylation agent in an appropriate solvent for a period of from 5 minutes to 3 hours or is stirred at ambient temperature for 4 to 16 hours.

After the preparation of the peracylated dihydroresorufin derivatives, the two O-acyl groups must be split off selectively. The selective cleavage of the resorufin ester bonds is achieved by reaction with 2 to 10 mole and preferably with 2 to 4 mole of sodium sulphite in a mixture of water and a water-soluble solvent, for example 1,4-dioxan, methanol or ethanol and preferably with a mixture of equal parts by volume of water and 1,4-dioxan. The reaction temperature is from 20° to 100° C. and preferably from 80° to 100° C. Under these reaction conditions, the N-acyl-dihydroresorufins can be prepared in high yields.

The N-acyl-resorufins so prepared can then be reacted with a compound of the general formula (VI) (X-A). In principle, this reaction takes place under the same conditions as have already been described for process variant a).

According to process variant (b), compounds of general formula (I) are especially prepared in which the substituents A and Z are $PO_3MM'$. For this purpose, the N-acyl-dihydroresorufin derivatives prepared as described above are reacted with a halide of pentavalent phosphorus, preferably in the presence of an inorganic or organic acid acceptor, and the dihalophosphonyloxy compound obtained is subsequently hydrolysed.

As halides of pentavalent phosphorus, there can be used, for example, phosphorus oxychloride, phosphorus pentachloride or pyrophosphoric acid tetrachloride, it being preferred to use phosphorus oxychloride or pyrophosphoric acid tetrachloride. It is quite especially preferred to use phosphorus oxychloride. As acid acceptors, there can be used inorganic and organic bases, for example alkali metal hydroxides, alkali metal carbonates, trialkylamines or pyridine.

The solvent can be the liquid organic acid acceptor used. However, as solvents or diluents there can also be used other liquids, especially organic liquids, for example chloroform, dichloromethane, acetonitrile or tetrahydrofuran.

The reaction is preferably carried out in the presence of a solvent or diluent at a temperature of from −30° to +20° C.

The hydrolysis of the dichlorophosphonyloxy compound formed as intermediate takes place gently at temperatures of from 0° to 20° C. by neutralisation with aqueous solutions of alkali metal hydroxides or carbonates, aqueous solutions of alkaline earth metal hydroxides, triethylamine or triethylammonium bicarbonate. The alkali metal, alkaline earth metal or ammonium salts obtained are concentrated in a vacuum and from the residue, there are obtained, by appropriate chromatographic processes, the desired diphosphoric acid dihydroresorufin derivative esters. Another method consists in precipitating out the diphosphoric acid ester from a concentrated aqueous solution of an alkali metal, alkaline earth metal or ammonium salt. The free diphosphoric acid derivatives can be obtained, for example, by acidification with mineral acids, such as hydrochloric acid, and subsequent precipitation.

For the synthesis of compounds of general formula (I) in which A, B and Z are all different one can start from compounds of tautomeric formula (II a) and (II b) in which $R^1$–$R^6$ have the above given meanings and Y means the group N→O. After reaction with a compound of general formula (VII)

X—A′          (VII)

in which
A′ has the meaning of A in general formula (I) or means a usual phenol protective group and
X is a reactive group,
the OH-substituted resazurin derivative is reduced and then isolated by a compound of general formula (V)

X—B          (V)

in which
B has the meaning given in general formula (I) and
X is a reactive group.
Then the OB ester bond is selectively hydrolysed and the resulting product is reacted with a compound of general formula (III)

$$X-Z \qquad (III)$$

in which
Z has the meaning given in general formula (I) and X is a reactive group.

If A' has not the meaning of A in general formula (I) it is removed in an appropriate manner. By reaction with a compound of general formula (VI)

$$X-A \qquad (VI)$$

in which
A has the meaning given in general formula (I) and X is a reactive group
the compound of general formula (I) in which A, B and Z are all different will then be obtained.

Reduction of the resazurin derivatives obtained after reaction with X—A' (VII) can be achieved in the same manner as already described for the reduction of resorufin derivatives of general formula (IV a) and (IV b). One must make sure however that such a reduction process is chosen that does not impair the OA' bond. This is especially important when A' is a phenol protective group which may be cleaved off hydrogenolitically, as may be done for example with the benzyl group.

In the process according to the invention every group A may be used as a group A', which will not be changed during the reaction sequence. But there may also be used a usual phenol protective group A', as for example a benzyl group, which will be replaced by A during the reaction sequence.

Reaction of the dihydroresorufin compound obtained after reduction of the OH substituted resazurin derivative can be achieved in such a manner with X—B (V) that only the amino group is selectively acetylated, so that subsequently the free OH group can be immediately reacted with X—Z (III). However a process if preferred in which both groups the amino group as well as the free hydroxy group are acetylated in one reaction step and in which subsequently the ester bond is selectively hydrolysed.

According to process variant (c), compounds of general formula (I) are especially prepared in which the substituent Z is an amino acid or oligopeptid residue which is bound ester like to the dihydroresorufin molecule. The amino groups or other functional groups of these residues may be free or blocked by usual protective groups. Especially preferred for the reaction are compounds X—Z (III) in which all functional groups of the amino acid or oligopeptide residues are protected. During the reaction sequence for the synthesis of compounds of general formula (I) in which A, B and Z are all different removal of these protective groups is possible. Very often it is not necessary however.

As a reactive group X in compounds of general formula (III) there may be used in this case all groups which are usual in peptide chemistry.

When in the compounds prepared according to process variant (c) Z is an amino acid or oligopeptide residue, A means preferably a lower alkyl carbonyl residue optionally substituted one or more times by carboxyl, hydroxyl and/or ammonium groups. Especially preferred is the glutaric acid or succinic acid residue.

In the preferred compounds B means a lower alkyl carbonyl residue. Especially preferred is the acetyl residue.

The especially preferred reactive group X in compounds of general formula (V) and (VI) are such which are usually used for the activation of carboxylic acids. Especially preferred are acid halogenides and acid anhydrides.

In compounds of general formula (VII) in which A' is a phenol protective group the reactive group X may be every group which can be reacted with phenolic hydroxy groups. Especially preferred are halogens. Quite specially preferred are chlorine and bromine.

In the case of the synthesis of compounds of general formula (I), there are obtained readily watersoluble, colourless and non-fluorescing compounds. Appropriate hydrolases are able to cleave the Z—O bond of such substrates and thus, depending upon whether Z is the same as or different from A, to liberate only N-acylated dihydroresorufin derivatives with two free hydroxyl groups or N-acylated dihydroresorufin derivatives with one free hydroxyl group. Such compounds liberated by the hydrolytic activities of the enzymes can easily be oxidised to give coloured and fluorescing resorufin derivatives which can readily be detected.

Thus a further subject of the present invention is the use of the compounds of general formula (I) for the detection and determination of hydrolases. Depending upon the choice of the substituents Z and A, the compounds according to the present invention of general formula (I) can, in principle, be used as substrates for all possible hydrolases. These compounds have proved to be especially advantageous as substrates for esterases and glycosidases.

Esterases cleaving carboxyl residues preferably react with compounds of general formula (I), in which Z is an alkylcarbonyl radical containing up to 20 carbon atoms or a carboxyl-bound amino acid or oligopeptide residue and A and B are lower alkylcarbonyl radicals which are optionally substituted one or more times by hydroxyl, carboxyl and/or ammonium. An appropriate substrate for the detection of a hydrolase cleaving fatty acid esters is, for example, a compound of general formula (I) in which Z is a propylcarbonyl radical and A and B are succinyl radicals, an especially preferred compound being N,3-disuccinyl-7-butyryl-3,7-dihydroxy-phenoxazine.

Carboxyl ester-cleaving enzymes which occur in leukocytes react especially well with compounds of general formula (I) in which Z is an amino acid or oligopeptide residue, for example alanine, and A and B are lower alkylcarbonyl radicals optionally substituted one or more times by carboxyl, hydroxyl and/or ammonium, for example acetyl, carnityl, succinyl or glutaryl radicals, N,3-disuccinyl-7-alanyl-3,7-dihydroxyphenoxazine, N,3-diglutaryl-7-alanyl-3,7-dihydroxyphenoxazine and N-acetyl-3-glutaryl-7-alanyl-3,7-dihydrophenoxazine being especially preferred. The amino group of the amino acid residue can hereby also be derivatised by conventional protective groups.

Acidic and alkaline phosphatases are also enzymes which are to be assigned to the esterase group. Compounds of general formula (I), in which Z is $PO_3MM'$ and A and B are lower alkylcarbonyl radicals which are optionally substituted one or more times by hydroxyl, carboxyl and/or ammonium, can be used as substrates for phosphatases of any origin. Compounds according to the present invention are preferred in which A and B are acetyl radicals, N,3-diacetyldihydroresorufin-7-phosphate being especially preferred as a phosphatase substrate.

However, for this purpose, compounds of general formula (I), in which A and Z are both phosphoric acid residues, can also be used for this purpose, especially preferred compounds including N-acetyl-dihydroresorufin-3,7-diphosphate and N-acetyl-2,8-dibromodihydroresorufin-3,7-diphosphate.

Glycosidase substrates are compounds of general formula (I) in which A and B are the same and signify lower alkylcarbonyl radicals which are optionally substituted one or more times by hydroxyl, carboxyl and/or ammonium and Z is a sugar residue. As sugar residue, there can, in principle, be used any mono- or oligosaccharide which can be split off from the dihydroresorufin basic structure by an appropriate glycosidase. Preferred monosaccharides are α- and β-glycosidically-bound glucose, galactose and mannose. Substrates which can be used for the detection of glucosidase are, for example, N,3-diacetyl-dihydroresorufin-7-glucoside, N,3-disuccinyl-dihydroresorufin-7-glucoside and N,3-diglutaryl-dihydroresorufin-7-glucoside, a preferred galactosidase substrate being, for example, N,3-diacetyl-dihydroresorufin-7-galactoside.

The products of the N,3-diacyl-dihydroresorufin derivatives resulting after enzymatic hydrolysis by oxidation and hydrolysis can be used not only for ultra-violet photometric and visual detection but especially also for fluorimetric measurement. This is of importance because, in comparison with photometric methods, the sensitivity of fluorimetric determinations is often increased by several powers of ten. In some cases, it is necessary to work with fluorogenic substrates, for example in the case of the investigation of enzyme activities in cells with the use of automatic apparatus for cell differentiation (cytofluorometry), as well as in the case of the analysis of immobilised enzymes, for example in flowthrough microfluorometry. In other cases, for example in the case of the determination of the enzyme labelling of test systems (enzyme immunoassays), which are often carried out with β-galactosidase but also with other hydrolases, the multiplication factor of the enzymatic catalysis is considerably increased by the use of fluorogenic substrates.

The great difference of the maximum absorption wavelength of substrate and resulting oxidised product has proved to be especially advantageous for the determination of hydrolases. All compounds of general formula (I) are colourless compounds, whereas the enzymatically hydrolysed and oxidised compounds are red to blue-red coloured.

Furthermore, there is to be especially stressed the good water-solubility of the compounds of general formula (I). The addition of organic solvents or of detergents to the enzymatic test in order to bring the chromogen used into solution thus becomes unnecessary. This advantage manifests itself, inter alia, in the case of kinetic enzyme tests where good solubilities of substrate and product are necessary and where solvent and detergent additions often influence the enzyme activities.

For the determination of hydrolases, a compound of general formula (I), an oxidation agent, an appropriate buffer system, as well as possibly further reagents and adjuvants, are mixed with the sample which contains the enzyme to be determined. In the case of the presence of the appropriate hydrolase, the N-acyldihydroresorufin derivatives of general formula (I) react to give a dihydroresorufin derivative with at least one free hydroxyl group which is then oxidised by the oxidation agent present. The change of the absorption or of the fluorescence intensity of the reaction mixture thereby brought about is measured photometrically or fluorimetrically. By a direct comparison with a standard solution or by indirect comparison with a standard curve, the content of the enzyme in the sample can thus be determined. Not only kinetic but also end point measurements are possible.

For the oxidation of the dihydroresorufin with at least one free hydroxyl group initially formed by the action of the hydrolase, there can be used any oxidation agent which does not influence the activity of the enzyme to be determined and which is strong enough to oxidise the resultant dihydroresorufin. Depending upon the substituents, for this purpose, even atmospheric oxygen can suffice. As a rule, as oxidation agent, there is used potassium ferricyanide, perborate, bilirubin oxidase or peroxidase/hydrogen peroxide.

The reagent for the determination of hydrolases contains, besides at least one substrate according to the present invention of general formula (I), an oxidation agent, an appropriate buffer system, as well as possibly further additives normally used for such reagents, for example further adjuvant enzymes, stabilisers and the like. The reagent according to the present invention can be in the form of a solution, lyophilisate, powder mixture or reagent tablet or can be applied to an appropriate carrier material.

The reagent according to the present invention in the form of a solution preferably contains all the reagents needed for the test. As solvent, there can be used water or a mixture of water with a water-soluble organic solvent, for example methanol, ethanol, acetone or dimethylformamide. For reasons of storage stability, it can be advantageous to divide the reagents needed for a test into two or more solutions which are first mixed together when carrying out the actual investigation.

For the preparation of a reagent in the form of a lyophilisate with a total weight of from about 5 to 20 mg. and preferably of about 10 mg., a solution is dried which, besides all the reagents needed for the test, contains conventional structure formers, for example polyvinylpyrrolidone, and possibly further filling materials, for example mannitol, sorbitol or xylitol.

A reagent in the form of a powder mixture or reagent tablet can be prepared by mixing the components of the test with conventional galenical additives and granulating. Additives of this kind include, for example, sugar alcohols, such as mannitol, sorbitol or xylitol, or other soluble, inert compounds, such as polyethylene glycols or polyvinylpyrrolidone. The powder mixtures or reagent tablets have, in general, an end weight of about 30 to 200 mg. and preferably of from 50 to 80 mg.

For the preparation of the reagent in the form of test strip, an absorbent carrier, preferably filter paper, cellulose or synthetic fibre fleece, is impregnated with solutions of the required reagents usually employed for the production of test strips in readily volatile solvents, for example water, methanol, ethanol or acetone. This can take place in one impregnation step. However, it is often desirable to carry out the impregnation in several stages, solutions thereby being used each of which contains a part of the components of the reagent. Thus, for example, in a first step, impregnation can be carried out with an aqueous solution which contains the oxidation agent, the buffer and other water-soluble additives and then, in a second step, with a solution which contains the hydrolase substrate. The finished test strips can be used as such or stuck in known manner to handles or preferably sealed between synthetic resins and fine meshes according to Federal Republic of Germany patent specification No. 21 18 455.

The following Examples illustrate some of the numerous process variants which can be used for the synthesis of the compounds according to the present invention, as well as, by way of example, the use of the new hydrolase substrates for the determination of the activity of appropriate hydrolases:

EXAMPLE 1

N-Acetyl-dihydroresorufin-3,7-diphosphate tetrasodium salt

(a) Triacetyl-3,7-dihydroxyphenoxazine 2.51 g. (10 mmole) resazurin sodium salt and 4.17 g. (22 mmole) stannous chloride were heated under reflux for 1 hour in a mixture of 6.7 ml. (72 mmole) acetic anhydride and 8 ml. glacial acetic acid, a clear brown solution gradually being formed. About 30 ml. methanol were then added thereto in an ice bath, while stirring, spontaneous crystallisation thereby taking place. After 20 hours at 0° C., the crystals were filtered off with suction, washed with ice cold isopropanol and petroleum ether and dried in a vacuum over anhydrous calcium chloride. There were obtained 2.64 g. (77% of theory) of beige coloured needles; m.p. 208° C. Rf value: 0.45 (TLC on silica gel; chloroform/ethyl acetate 2:1 v/v).

(b) N-Acetyl-3,7-dihydroxyphenoxazine 2.39 g. (7 mmole) Triacetyl-3,7-dihydroxyphenoxazine and 1.9 g. (15 mmole) sodium sulphite were dissolved in 70 ml. of a dioxan-water mixture (1:1 v/v) which had been gassed with nitrogen and heated under reflux for 20 minutes. The reaction mixture was then cooled in an ice bath, acidified with 1.14 ml. (20 mmole) acetic acid, filtered off over a wadding from a small amount of insoluble material and concentrated to about 20 ml., a viscous oil hereby separating out. About 150 ml. water, which had been gassed with nitrogen, were added thereto and the mixture left to stand at 0° C. The precipitated crystals were filtered off with suction, washed with ice water and dried in a vacuum at 0° C. over anhydrous calcium chloride. Yield 1.5 g. (97% of theory) of a beige coloured product; m.p. >250° C. (decomp.).

Rf value: 0.19 (TLC on silica gel; chloroform/ethyl acetate 2:1 v/v).

(c) N-Acetyl-dihydroresorufin-3,7-diphosphate tetrasodium salt

A mixture of 1.29 g. (5 mmole) N-acetyl-dihydroresorufin and 1.62 ml. (20 mmole) phosphorus oxychloride in 5 ml. anhydrous tetrahydrofuran was added dropwise at 0° C., while stirring and within the course of 20 minutes, to 10 ml. anhydrous pyridine. The ice bath was removed and the reaction mixture stirred at ambient temperature for a further 2 hours. The reaction mixture was then poured on to 50 g. of ice and after 3 hours concentrated to about 20 ml., adjusted with 2N aqueous sodium hydroxide solution to pH 8 and left to crystallise out overnight at 0° C. The product was filtered off with suction, washed with a little ice water, isopropanol and petroleum ether and dried to constant weight. Yield 1.5 g. (59% of theory) of colourless powder. Rf value: 0.71 (TLC on cellulose, 1M aqueous ammonium acetate solution/ethanol 5:2 v/v).

EXAMPLE 2

N-Acetyl-2,8-dibromo-dihydroresorufin-3,7-diphosphate tetralithium salt

(a) Triacetyl-2,8-dibromo-dihydroresorufin 7.4 g. (20 mmole) 2,8-Dibromoresorufin (see G. B. Afanasieva et al., Khim. Geterotsek L. Soedin, 1974, pp. 348–353) were catalytically hydrogenated in a mixture of 150 ml. glacial acetic acid and 50 ml. acetic anhydride with the addition of 0.8 g. palladium on charcoal (10%) until the theoretical amount of hydrogen had been taken up. The reaction mixture was vigorously flushed with oxygen-free nitrogen and heated under reflux for 1 hour with the exclusion of moisture. The reaction mixture was filtered hot and evaporated to dryness in a vacuum. Yield 3.5 g. of colourless crystals.

(b) N-Acetyl-2,8-dibromodihydroresorufin 3.5 g. (7 mmole) Triacetyl-2,8-dibromodihydroresorufin were taken up in 30 ml. dioxan, mixed with a solution of 0.95 g. sodium sulphite (7.5 mmole) in 30 ml. water and heated under reflux for 20 minutes. The reaction mixture was evaporated to dryness in a vacuum and homogenised with about 80 ml. ice water. The precipitate was filtered off with suction, washed with ice water and dried. Yield 2.15 g. (74% of theory) of a light grey powder; m.p. 189°–190° C.

(c) N-Acetyl-2,8-dibromodihydroresorufin-3,7-diphosphate tetralithium salt 2 g. (4.8 mmole) N-Acetyl-2,8-dibromodihydroresorufin were dissolved in 50 ml. anhydrous pyridine and a mixture of 1.77 ml. (19.3 mmole) phosphorus oxychloride and 30 ml. anhydrous pyridine added dropwise thereto within the course of 2 hours at 0° C. The reaction mixture was allowed to warm up to ambient temperature and further stirred for 1 hour. The mixture was poured on to 100 g. ice, adjusted to pH 8 with 2N aqueous lithium hydroxide solution, suction filtered from lithium phosphate and concentrated in a vacuum to 50 ml. It was chromatographed over 1.7 liters Sephadex LH 20 (50% methanol) and fractioned in 10 ml. portions. The phosphatase-positive fractions were combined and evaporated to dryness in a vacuum. The residue was digested with 200 ml. acetone, filtered off with suction and dried. Yield 2.75 g. (95% of theory). Rf value: 0.57 (TLC on cellulose, 1M aqueous ammonium acetate solution/ethanol 5:2 v/v).

EXAMPLE 3

Determination of the activity of acidic phosphatase

N-Acetyl-2,8-dibromodihydroresorufin-3,7-diphosphate tetralithium salt was dissolved in a concentration of 1 mmole/liter in 0.1M citrate buffer (pH 5.2) containing 0.1 mmole potassium ferricyanide/liter.

0.20 ml. serum containing acidic phosphatase was added to 2.00 ml. of this solution in a cuvette. The mixture was incubated for 5 minutes at 30° C., then the initial extinction was read off at a measurement wavelength of 578 nm and this reading off repeated after precisely 1, 2 and 3 minutes. From the extinction differences per minute ($\Delta E$/min.) there was obtained an average value and this used in the equation for the calculation of the enzyme activity. The activity of the acidic phosphatase is calculated as follows:

$$U/l. = \frac{1000 \times V}{\epsilon \times d \times v} \times \Delta E/\text{min}.$$

U/l. = activity of the enzyme in units per liter

V = total volume in ml.

v = sample volume in ml.

$\epsilon$ = extinction coefficient of the indicator substance in $l \cdot \text{mmole}^{-1} \cdot \text{cm}^{-1}$ d = layer thickness of the cuvette in cm.

EXAMPLE 4

Determination of alkaline phosphatase

N-Acetyldihydroresorufin-3,7-diphosphate tetrasodium salt was dissolved in a concentration of 1 mmole/liter in 0.1M diethanolamine buffer (pH 9.8) containing 0.1 mmole potassium ferricyanide/liter. Upon adding a solution which contained alkaline phosphatase, a colour change took place from colourless to blue-red. The intensity of the coloration is proportional to the concentration of the alkaline phosphatase in the sample. With the help of samples of known concentration of alkaline phosphatase, a calibration curve can be obtained on the basis of which can be determined the unknown phosphatase content of a sample.

EXAMPLE 5

7,10-Diacetyl-3,7-dihydroxyphenoxazine-3-phosphate lithium salt (a) O-Acetylresorufin A mixture of 21.3 g. (0.1 mole) resorufin, 50 ml. acetic anhydride and 25 ml. glacial acetic acid was heated under reflux for 4 hours. The reaction mixture was left to stand overnight at 0° C., the resultant crystal slurry was stirred up with diethyl ether/petroleum ether (1:1 v/v) and the crystals filtered off with suction. The crystals were afterwashed with petroleum ether and dried in a vacuum over anhydrous calcium chloride at 60° C. Yield 18.5 g. (72.5% of theory) of orange coloured crystals; m.p. 185°–190° C.

(b) N,O-Diacetyldihydroresorufin 12.8 g. (50 mmole) O-Acetylresorufin, 5.7 ml. (60 mmole) acetic anhydride and 0.6 g. palladium on charcoal were hydrogenated for 6 hours in 120 ml. glacial acetic acid. The mixture was diluted with water, left to stand for 5 hours at 0° C. and the crystals then filtered off with suction. The crystals were dissolved in acetone and filtered off from the catalyst. The solution was mixed with water, concentrated and left to stand for 20 hours at 0° C. The crystals formed were filtered off with suction, washed with water and dried in a vacuum at 50° C. over anhydrous calcium chloride. Yield 14.6 g. (97.5% of theory) of crystals; m.p. 182° C.

(c) 7,10-Diacetyl-3,7-dihydroxyphenoxazine-3-phosphate, lithium salt 1.5 g. (5 mmole) N,O-Diacetyldihydroresorufin was dissolved in a mixture of 1.53 g. (0.92 ml., 10 mmole) phosphorus oxychloride, 5.6 ml. (70 mmole) anhydrous pyridine and 20 ml. anhydrous dioxan and stirred for 20 hours at ambient temperature. The mixture was poured on to 50 g. of ice, the aqueous solution was applied to 240 ml. DEAE-Sephadex ® and fractionally chromatographed with 0.5N aqueous lithium chloride solution. The combined product fractions were evaporated, mixed twice with, in each case, 200 ml. acetone, homogenised, filtered off with suction and dried in a vacuum over anhydrous calcium chloride. The product was applied with water to 1.2 liters Diaion ® and eluted with the addition of isopropanol. Yield 1.42 g. (74% of theory) of a pale grey powder.

EXAMPLE 6

N,O-Diacetyldihydroresorufin-D-galactopyranoside (a) N,O-Diacetyldihydroresorufin-2,3,4,6-tetra-O-benzyl-D-galactopyranoside A solution of 6.8 g. (10.0 mmole) O-(2,3,4,6-tetra-O-benzyl-D-galactopyranosyl)-trichloroacetimidate (synthesis according to Angewandte Chemie, 92, 763/1980), 1.5 g. (5.0 mmole) N,O-diacetyldihydroresorufin and 1.7 g. (12.0 mmole) boron trifluoride etherate in 30 ml. anhydrous dichloroethane was stirred under reflux for 6 hours. The reaction mixture was allowed to cool to 20° C. and the reaction solution shaken out with 100 ml. of a 1M aqueous solution of sodium hydrogen carbonate. The organic phase was dried over anhydrous sodium sulphate and evaporated in a vacuum. The product thus obtained was purified by column chromatography on silica gel (flash chromatography, eluent chloroform/petroleum ether 8/2 v/v). Yield (anomeric mixture) 1.5 g. (36% of theory, referred to the N,O-diacetyldihydroresorufin).

Rf (silica gel; chloroform/ethyl acetate 9:1 v/v)=0.63. MS: m/e=821.

(b) N,O-Diacetyldihydroresorufin-D-galactopyranoside

For splitting off the benzyl protective group, 1.5 g. (1.8 mmole) N,O-diacetyldihydroresorufin-2,3,4,6-tetra-O-benzyl-D-galactopyranoside was dissolved in 70 ml. dichloromethane and, after the addition of 3 g. palladium sponge, hydrogenated at normal pressure. The reaction was ended after about 2 hours. After separating off the catalyst, the reaction solution was evaporated in a vacuum and the crude product thus obtained was purified by column chromatography on silica gel (flash chromatography; eluent chloroform/ethyl acetate 9:1 v/v) and the solvent removed in a vacuum. Yield 100 mg. (12% of theory). Rf (silica gel, chloroform/methanol=8:2 v/v)=0.33 MS (pos. FAB): m/e=462, MS (neg. FAB): m/e=460.

EXAMPLE 7

7,10-Disuccinyl-3,7-dihydroxyphenoxazine-3-butyrate (a) Resorufin-O-butyrate 2.13 g. (10 mmole) Resorufin were dissolved in a mixture of 8 ml. (50 mmole) butyric anhydride and 5 ml. absolute dimethylformamide and stirred for 20 hours at 50° C. with the exclusion of moisture. The mixture was then evaporated in a vacuum and mixed with petroleum ether, crystallisation thereby taking place. The crystals were recrystallised from aqueous acetone. Yield 3.15 g. (85% of theory) of orange coloured needles; m.p. 133°–134° C.

(b) 7,10-Disuccinyl-3,7-dihydroxyphenoxazine-3-butyrate 3 g. Resorufin-O-butyrate were dissolved in 50 ml. anhydrous tetrahydrofuran and mixed with 1.8 g. succinic anhydride, 1.7 g. stannous chloride, 0.5 ml. glacial acetic acid and a spatula tip of 4-(N,N-dimethylamino)-pyridine. The reaction mixture was stirred for 12 hours at 80° C. and then evaporated to dryness. The residue was recrystallised from ethanol.

Yield: 2 g. of colourless crystals
Rf (silicagel, chloroform/ethyl acetate=2:1 v/v)=0.45.

EXAMPLE 8

O-(N'-Tos-Ala)-N-acetyl-O-glutaryldihydroresorufin (a) O-Benzylresazurin

A solution of 25.1 g. (0.1 mole) resazurin sodium salt, 8.4 g. (0.1 mole) sodium hydrogen carbonate, 1.6 g. (0.01 mole) potassium jodide and 14.3 ml. (0.12 mole) benzylbromide in 300 ml. dimethylformamide was stirred at 100° C. for 22 hours.

After cooling off the reaction solution was poured into 2 l. ice water and the precipitated product was filtered off after 2 hours. Then the filtrate was washed with ice water until it was colourless. The product was dried at 35° C. over anhydrous calcium chloride in a vacuum.

Yield: 20.5 g. (64% of theory),
m.p.: 205°-207° C. (decomposition),
Rf (silicagel, chloroform:acetone=7:3 v/v)=0.75.

(b) N,O-Diacetyl-O-benzyl-dihydroresorufin

To a solution of 10 g. (31 mmole) O-benzylresazurin in 250 ml. absolute acetic acid were slowly added with stirring 22 g. (336 mmole) zinc powder. The reaction mixture was heated to reflux for one hour. After cooling off 100 ml. acetic anhydride were slowly dropped to this mixture. Then the reaction mixture was again heated to reflux for five hours. After cooling off the undissolved was filtered off and the filtrate was concentrated in a vacuum. The residue was then dissolved in ethyl acetate, extracted with 5% sodium hydrogen carbonate solution and water and the organic phase was dried over anhydrous sodium sulphate. After removing the solvent the crude product was crystallized from toluene.

Yield: 6.4 g. (53% of theory)
m.p.: 134°-136° C.
Rf (silicagel, chloroform:acetone=7:3 v/v)=0.87.

(c) N-Acetyl-O-benzyl-dihydroresorufin

A solution of 2.25 g. (17.5 mmole) sodium sulphite in 150 ml. water was added at 20° C. to a solution of 6.2 g. (16 mmole) N,O-diacetyl-O-benzyl-dihydroresorufin in 150 ml. dioxan. The reaction mixture was heated to 90° C. for one hour. After cooling off the mixture was extracted several times with ethylacetate. The organic phase was dried over anhydrous sodium sulphate. The solvent was removed in vacuo. Purification of the crude product was achieved by column chromatography with silicagel (eluent chloroform:acetone=7:3 v/v).

Yield: 4.3 g. (78% of theory),
m.p.: 170°-180° C. (oxidation),
Rf (silicagel, chloroform:acetone=7:3 v/v)=0.79.

(d) O-(N'-Tos-Ala)-N-acetyl-O-benzyldihydroresorufin 3.47 g. (10 mmole) N-Acetyl-O-benzyldihydroresorufin were dissolved in 10 ml. anhydrous tetrahydrofuran and mixed successively at 0° C., with the exclusion of moisture and while stirring, with 3.93 g. (15 mmole) of toluenesulphonyl-protected acid chloride of alanine and 2.1 ml. (15 mmole) triethylamine and stirred for 18 hours at ambient temperature. The resultant triethylamine hydrochloride was filtered off with suction and the solution evaporated to dryness in a vacuum, the product being obtained in the form of a resin.

Rf=0.51 (chloroform/ethyl acetate 2:1 v/v).

(e) O-(N'-Tos-Ala)-N-acetyl-O-glutaryldihydroresorufin 5.9 g. O-(N'-Tos-Ala)-N-acetyl-O-benzylresorufin were dissolved in 20 ml. tetrahydrofuran and mixed with 0.6 g. palladium on charcoal. The reaction mixture was heated to the boil and a constant stream of hydrogen passed in over the course of 6 hours. After cooling, the solution was filtered, mixed with 1.4 g. glutaric anhydride and a spatula tip of 4-(N,N-dimethylamino)-pyridine and heated under reflux for a further 18 hours. The reaction mixture was then evaporated to dryness. Purification of the crude product was achieved by column chromatography with silicagel (eluent chloroform::ethyl acetate=3:1 v/v).

Yield: 3.5 g. colourless crystals,
Rf (silicagel, chloroform:ethyl acetate=2:1 v/v)=0.27.

It will be understood that the specification and examples are illustrative but not limitative of the present invention and that other embodiments within the spirit and scope of the invention will suggest themselves to those skilled in the art.

We claim:

1. A compound of the formula

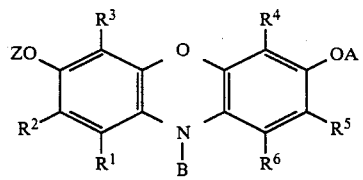

wherein
one of Z and A is an orthophosphoric or a pyrophosphoric acid residue or a sulphuric acid residue;
the other of Z and A is an orthophophosphoric, pyrophosphoric or a sulphuric acid residue; a saturated or unsaturated ($C_1$–$C_{20}$)-alkylcarbonyl; an amino acid or an oligopeptide residue bound by their carboxylic acid ends; or, if Z is an orthophosphoric, pyrophosphoric or sulphuric acid residue, A may also be ($C_1$–$C_7$)-alkylcarbonyl, optionally unsaturated, which is substituted one or more times by hydroxyl, carboxyl or an ammonium group;
B is a ($C_1$–$C_7$)-alkylcarbonyl optionally substituted one or more times by hydroxyl, carboxyl or an ammonium group;
each of $R^2$ and $R^5$ is hydrogen, halogen or ($C_1$–$C_5$)-alkyl;
each of $R^1$, $R^3$, $R^4$ and $R^6$ is hydrogen; halogen, cyano; ($C_1$–$C_5$)-alkyl; ($C_1$–$C_5$)-alkoxy; carboxyl; ($C_1$–$C_5$)-alkoxycarbonyl; carboxy-($C_1$–$C_5$)-alkyl;

($C_1$–$C_5$)-alkoxycarbonyl-($C_1$–$C_5$)-alkyl; carboxamido optionally substituted once or twice by ($C_1$–$C_5$)-alkyl, ($C_1$–$C_5$)-alkoxy-($C_1$–$C_5$)-alkyl, carboxy-($C_1$–$C_5$)-alkyl or ($C_1$–$C_5$)-alkoxycarbonyl-($C_1$–$C_5$)-alkyl), or in the case of disubstitution, the two substitutents can be joined to form a ring which can be interrupted by oxygen, nitrogen and sulphur atoms; or a radical of the formula $$-COO-(CH_2CH_2O)_n-R^7$$

in which $R^7$ is a hydrogen or ($C_1$–$C_5$)-alkyl, and n is a whole number of from 1 to 4; and $R^6$ can also be sulpho or nitro.

2. A compound according to claim 1, wherein Z is the residue $PO_3MM'$ or $SO_3M$ in which M and M' are hydrogen, alkali metal ions selected from the group consisting of lithium, sodium and potassium, alkaline earth metal ions selected from the group consisting of magnesium, calcium and barium, or ammonium ions optionally substituted one or more times by ($C_1$–$C_5$)-alkyl or benzyl; a residue of acetic acid, propionic acid, butyric acid, palmitic acid, stearic acid, oleic acid, linoleic acid or linolenic acid; a residue of an alpha-amino acid selected from the group consisting of glycine, alanine, valine, leucine, isoleucine, phenylalanine and thyrosine, in their L-, D- or racemic forms or a residue of a di-, tri-, tetra-, or penta-peptide composed of said alpha-amino acids.

3. A compound according to claim 2, in which Z is the residue $PO_3MM'$ in which M and M' are hydrogen, said alkali metal ions, said alkaline earth metal ions or an ammonium ion optionally substituted one or more times by methyl or ethyl; a residue of acetic acid, propionic acid, butryic acid, palmitic acid, stearic acid, oleic acid, linoleic acid or linolenic acid; a residue of said alpha-amino acids in their L-form; or a residue of a di- or tri-peptide of said alpha-amino acids in their L-form.

4. A compound according to claim 3, in which the alpha-amino acids are in their L-form having their free amino groups protected by acylation, and
the peptide residues are di- or tri-peptides, in which the free amino groups in the alpha-amino acids are protected by acyl, oxycarbonyl, thiocarbonyl, sulpho, sulphino, vinyl, cyclohexenyl, phosphoryl, carbamoyl, tosyl, benzyloxycarbonyl or tert.-butoxycarbonyl groups.

5. A compound according to claim 1, in which A is the residue $PO_3MM'$ or $SO_3M$ in which M and M' are hydrogen, alkali metal ions selected from the group consisting of lithium, sodium and potassium, alkaline earth metal ions selected from the group consisting of magnesium, calcium and barium, or ammonium ions optionally substituted one or more times by ($C_1$–$C_5$)-alkyl or benzyl; a residue of acetic acid, propionic acid, butyric acid, palmitic acid, stearic acid, oleic acid, linoleic acid or linolenic acid; a residue of an alpha-amino acid selected from the group consisting of glycine, alanine, valine, leucine, isoleucine, phenylalanine and throsine, in their L-, D- or racemic form; or a residue of a di-, tri-, tetra- or penta-peptide of said alpha-amino acids; or a ($C_1$–$C_5$)-alkylcarbonyl, optionally unsaturated which is substituted one or more times by hydroxyl, carboxyl or an ammonium group which is optionally substituted one or more times by ($C_1$–$C_5$)-alkyl or benzyl.

6. A compound according to claim 5, in which the alpha-amino acids are in their L-form having their free amino groups protected by acylation,
the peptide residues are the di- or tri-peptides of said alpha-amino acids in their L-form; the free amino groups of the alpha-amino acids are protected by acyl, oxycarbonyl, thiocarbonyl, sulpho, sulphino, vinyl, cyclohexenyl, phosphoryl, carbamoyl, tosyl, benzyloxycarbonyl or tert.-butoxy carbonyl groups,
the ($C_1$–$C_5$)-alkylcarbonyl group is substituted by carboxyl.

7. A compound according to claim 1, in which B is ($C_1$–$C_5$)-alkylcarbonyl optionally unsaturated or substituted by hydroxyl, carboxyl or an ammonium group which is optionally substituted one or more times by ($C_1$–$C_5$)-alkyl or benzyl.

8. A compound according to claim 1, in which B is acetyl, oxalyl, malonyl, succinyl, glutaryl or carnityl.

9. A compound according to claim 2, in which A and B are the same.

10. A compound according to claim 1, in which
each of $R^2$ and $R^5$ is hydrogen, halogen or ($C_1$–$C_3$) alkyl; and
each of $R^1$, $R^3$, $R^4$ and $R^6$ is hydrogen; chlorine or bromine; cyano; ($C_1$–$C_3$)-alkyl; ($C_1$–$C_3$)-alkoxy; carboxyl, ($C_1$–$C_3$)-alkoxycarbonyl; carboxy-($C_1$–$C_3$)-alkyl; ($C_1$–$C_3$)-alkoxycarbonyl-($C_1$–$C_3$)-alkyl; carboxamido optionally substituted once or twice by ($C_1$–$C_3$)-alkyl, ($C_1$–$C_3$)-alkoxy-($C_1$–$C_3$)-alkyl, carboxy-($C_1$–$C_3$)-alkyl or ($C_1$–$C_3$)-alkoxycarbonyl-($C_1$–$C_3$)-alkyl, or in the case of disubstitution, the two substitutents can be joined to form a morpholine group; or a radical of the formula $$-COO-(CH_2CH_2O)_n-R^7$$

in which $R^7$ is hydrogen or ($C_1$–$C_3$)-alkyl, and n is a whole
number from 1 to 4.

11. A compound according to claim 10, in which the alkyl groups are methyl and the alkoxy groups are methoxy.

12. A compound according to claim 1, wherein one of Z and A is the residue $PO_3MM'$ or $SO_3M$ in which M and M' are hydrogen, alkali metal ions selected from the group consisting of lithium, sodium and potassium, alkaline earth metal ions selected from the group consisting of magnesium, calcium and barium, or ammonium ions optionally substituted one or more times by ($C_1$–$C_5$)-alkyl or benzyl;
the other of Z and A is the residue $PO_3MM'$ or $SO_3M$ in which M and M' are hydrogen, alkali metal ions selected from the group consisting of lithium, sodium and potassium, alkaline earth metal ions selected from the group consisting of magnesium, calcium and barium, or ammonium ions optionally substituted one or more times by ($C_1$–$C_5$)-alkyl or benzyl; a residue of acetic acid, propionic acid, butyric acid, palmitic acid, stearic acid, oleic acid, linoleic acid or linolenic acid; a residue of an alpha-amino acid selected from the group consisting of glycine, alanine, valine, leucine, isoleucine, phenylalanine and thyrosine, in their L-, D- or racemic form; or a residue of a di-, tri-, tetra- or penta-peptide of said alpha-amino acids;
or, if Z is the residue $PO_3MM'$ or $SO_3M$, A may also be a ($C_1$–$C_5$)-alkylcarbonyl group, optionally unsaturated, which is substituted one or more times by hydroxyl, carboxyl or an ammonium group which is optionally substituted one or more times by $(C_1-C_5)$-alkyl or benzyl;

B is $(C_1-C_5)$-alkylcarbonyl optionally unsaturated or substituted by hydroxyl, carboxyl or an ammonium group which is optionally substituted one or more times by $(C_1-C_5)$-alkyl or benzyl;

each of $R^2$ and $R^5$ is hydrogen, halogen or $(C_1-C_3)$-alkyl; and each of $R^1$, $R^3$, $R^4$ and $R^6$ is hydrogen; chlorine or bromine; cyano; $(C_1-C_3)$-alkyl; $(C_1-C_3)$-alkoxy; carboxyl, $(C_1-C_3)$-alkoxy-carbonyl; carboxy-$(C_1-C_3)$-alkyl; $(C_1-C_3)$-alkoxycarbonyl-$(C_1-C_3)$-alkyl; carboxamido optionally substituted once or twice by $(C_1-C_3)$-alkyl, $(C_1-C_3)$-alkoxy-$(C_1-C_3)$-alkyl, carboxy-$(C_1-C_3)$-alkyl or $(C_1-C_3)$-alkoxycarbonyl-$(C_1-C_3)$-alkyl, or in the case of disubstitution, the two substitutents can be joined to form a morpholine group; or a radical of the formula $$-COO-(CH_2CH_2O)_n-R^7$$

in which $R^7$ is hydrogen or $(C_1-C_3)$-alkyl, and n is a whole number from 1 to 4.

13. The compound according to claim 1, which is N-acetyl-dihydroresorufin-3,7-diphosphate tetrasodium salt.

14. The compound according to claim 1, which is N-acetyl-2,8-dibromo-dihydroresorufin-3,7-diphosphate tetralithium salt.

15. The compound according to claim 1, which is 7,10-diacetyl-3,7-dihydroxyphenoxazine-3-phosphate lithium salt.

* * * * *